United States Patent
Nakano

(10) Patent No.: US 6,683,411 B2
(45) Date of Patent: Jan. 27, 2004

(54) DISCHARGE LAMP, ULTRAVIOLET RAY IRRADIATION APPARATUS AND METHOD OF USING THE APPARATUS

(75) Inventor: Koji Nakano, Hachioji (JP)

(73) Assignee: Photoscience Japan Corporation (JP)

( * ) Notice: Subject to any disclaimer, the term of this patent is extended or adjusted under 35 U.S.C. 154(b) by 0 days.

(21) Appl. No.: 09/998,804

(22) Filed: Nov. 13, 2001

(65) Prior Publication Data

US 2002/0190227 A1 Dec. 19, 2002

(30) Foreign Application Priority Data

Jun. 14, 2001 (JP) ........................ 2001-179972

(51) Int. Cl.$^7$ .................... H01J 17/00; H01J 61/00; H01J 17/16; G21G 4/00
(52) U.S. Cl. .................. 313/571; 313/567; 313/621; 313/315; 313/316; 313/634; 313/636; 250/365; 250/493.1; 250/494.1; 250/504 H; 250/504 R
(58) Field of Search .................. 250/504 R, 365, 250/493.1, 494.1, 504 H; 313/39, 315, 316, 571, 567, 621, 634, 636; 314/7; 376/248; 427/553; 445/73

(56) References Cited

U.S. PATENT DOCUMENTS

| 4,074,164 A | * | 2/1978 | Leyendecker | 313/25 |
| 4,366,408 A | * | 12/1982 | Cooper et al. | 313/39 |
| 5,187,413 A | * | 2/1993 | Araki et al. | 315/291 |
| 5,266,362 A | * | 11/1993 | Katoh et al. | 427/553 |
| 5,569,979 A | * | 10/1996 | Scott et al. | 313/636 |
| 5,889,367 A | * | 3/1999 | Hofmann et al. | 313/634 |
| 5,912,934 A | * | 6/1999 | Acks et al. | 376/248 |
| 6,188,179 B1 | * | 2/2001 | Boys et al. | 315/244 |

FOREIGN PATENT DOCUMENTS

| JP | 5-50061 A | 3/1993 |
| JP | 5-258718 A | 10/1993 |
| JP | 7-21982 A | 1/1995 |
| JP | 10-151448 A | 6/1998 |
| JP | 10-208700 A | 8/1998 |
| JP | 2000-357491 A | 12/2000 |

* cited by examiner

Primary Examiner—John R. Lee
Assistant Examiner—Mary El-Shammaa
(74) Attorney, Agent, or Firm—Rossi & Associates

(57) ABSTRACT

Discharge lamp includes a synthetic quartz glass tube having an inside diameter of 8 mm or over and a pair of filaments provided within and at opposite ends of the glass tube with an L (cm) filament-to-filament distance, and rare gas and metal including at least mercury are sealed in the interior of the glass tube. Lamp voltage V (V) and lamp current I (A) during illumination of the discharge lamp, filament-to-filament distance L (cm) and inside diameter D (cm) of the glass tube have relationship represented by the following mathematical expression. Namely, $(V-Vf)/L = X/(\sqrt{D} \cdot \sqrt{I})$ and $2.6 \leq X \leq 4.2$, where Vf is a constant factor depending solely on a illuminating power source and where that if the discharge lamp is illuminated by a high-frequency power source of 1 kHz or over, Vf is 10, but if the discharge lamp is illuminated by a power source of 1 kHz or below, Vf is 50.

3 Claims, 6 Drawing Sheets

DISCHARGE LAMP, ULTRAVIOLET RAY IRRADIATION APPARATUS AND METHOD OF USING THE APPARATUS

BACKGROUND OF THE INVENTION

The present invention relates to an improved discharge lamp which radiates ultraviolet energy of a short wavelength range, and an improved ultraviolet ray irradiation apparatus using such a discharge lamp. The present invention is suitable for use in the fields of decomposition, sterilization, disinfection, etc. of organic substances.

Ultraviolet rays of short wavelengths less than 220 nm are being used today in various fields and various applications, such as decomposition of harmful substances and organic substances. FIG. 6 shows an example of a conventionally-known closed-type liquid treating or processing ultraviolet ray irradiation apparatus, where at least one discharge lamp 30 enclosed in an outer tube (protective tube) 20 is accommodated in a cylinder 1 made of stainless steel. Liquid to be treated or processed is introduced into the cylinder 1, so that ultraviolet rays are irradiated from the discharge lamp 30 onto the introduced liquid to be processed. For example, the discharge lamp 30 used here is a low-pressure mercury vapor discharge lamp that radiates ultraviolet rays of a 185 nm wavelength (hereinafter also referred to as "185 nm-wavelength ultraviolet rays"). Light-emitting bulb 10 of the discharge lamp 30 is made of quartz glass having good transmissivity with respect to ultraviolet rays. The discharge lamp 30 is enclosed in the outer tube (protective tube) 20 transmissive to ultraviolet rays, so as to be isolated from the to-be-processed liquid in a liquid-tight manner. The outer tube 20 too is made of quartz glass having good transmissivity with respect to ultraviolet rays. The cylinder 1 is closed at its opposite ends with flanges 1a and 1b, and the to-be-processed liquid introduced via a liquid inlet 1c is subjected to irradiation of ultraviolet rays as it passes through the cylinder 1, and then discharged through a liquid outlet 1d. A plurality of (five in the illustrated example) reflux or baffle plates 1e–1i are provided within the cylinder 1 between the liquid inlet 1c and the liquid outlet 1d, so as to prevent a short pass of the to-be-processed liquid flowing from the liquid inlet 1c toward the liquid outlet 1d. Note that although the liquid processing ultraviolet ray irradiation apparatus is shown in FIG. 6 as including only one discharge lamp 30 for convenience of illustration, a large-capacity apparatus equipped with a plurality of the discharge lamps 30 is often used in actual cases. Ultraviolet rays emitted from the discharge lamp 30 pass through the outer tube 20 to be irradiated onto the to-be-processed liquid. For example, the irradiated ultraviolet rays function to decompose any organic substances present in the liquid into harmless carbon monoxide (CO), carbon dioxide ($CO_2$) and water ($H_2O$) as represented by the following mathematical expressions:

$H_2O + h\nu(185\ nm) \rightarrow H + OH$ radical $C_n H_m O_k + OH\ radical \rightarrow CO, CO_2\ and\ H_2O$ where n, m and k represent 1, 2, 3, . . . .

The low-pressure mercury vapor discharge lamp, known as a source for emitting short-wavelength ultraviolet rays, has hitherto been applied primarily as a fluorescent lamp or sterilizing lamp. The fluorescent lamp is a discharge lamp that converts ultraviolet rays of 254 nm wavelength into visible light by means of a fluorescent substance, and the sterilizing lamp is a discharge lamp that utilizes ultraviolet rays of 254 nm wavelength. While a variety of in-depth studies have been made of the irradiation of the 254 nm-wavelength ultraviolet rays, it can not be said that the 185 nm-wavelength ultraviolet rays have attracted sufficient people's attention or have been studied sufficiently up to the present time.

SUMMARY OF THE INVENTION

In view of the foregoing, it is an object of the present invention to provide an improved discharge lamp which can irradiate 185 nm-wavelength ultraviolet rays with an enhanced radiation efficiency and keep the enhanced radiation efficiency of the ultraviolet rays to thereby permit significant savings in energy and maintenance, as well as an ultraviolet ray irradiation apparatus using the improved discharge lamp and a method for using the ultraviolet ray irradiation apparatus.

In order to accomplish the above-mentioned object, the present invention provides a discharge lamp comprising a synthetic quartz glass tube having an inside diameter of 8 mm or over, and a pair of filaments provided within and at opposite ends of the glass tube with an L (cm) filament-to-filament distance, a mixture of rare gas and metal including at least mercury being sealed in an interior of the glass tube. In this discharge lamp, a lamp voltage V (V) and lamp current I (A) during illumination of the discharge lamp, filament-to-filament distance L (cm) and inside diameter D (cm) of the glass tube have relationship represented by the following mathematical expression:

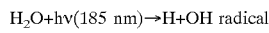
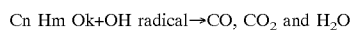

$(V-Vf)/L = X/(\sqrt{D} \cdot \sqrt{I})$ and $2.6 \leq X \leq 4.2$, where Vf is a constant factor depending on a illuminating power source and where if the discharge lamp is illuminated by a high-frequency power source of 1 kHz or over, Vf is 10, but if the discharge lamp is illuminated by a power source of 1 kHz or below, Vf is 50.

As will be later detailed in relation to embodiments of the present invention, the invention advantageously allows a low-pressure mercury vapor discharge lamp to radiate ultraviolet rays of a 185 nm wavelength with an enhanced efficiency and have longer life, by setting the various conditions as represented by the above-mentioned mathematical expression.

According to another aspect of the present invention, there is provided an ultraviolet ray irradiation apparatus using the novel discharge lamp arranged in the above-mentioned manner, which comprises a processing apparatus that irradiates ultraviolet rays, emitted by the discharge lamp, onto an object to be processed. Because the ultraviolet ray irradiation apparatus employs the discharge lamp capable of radiating the 185 nm-wavelength ultraviolet rays with an enhanced efficiency and having prolonged life, the irradiation apparatus can be an energy-saving type apparatus capable of operating at greatly reduced running costs.

According to still another aspect of the present invention, there is provided a method of using the ultraviolet ray irradiation apparatus arranged in the above-mentioned manner, which comprises: installing a plurality of the discharge lamps in the processing apparatus; deilluminating a predetermined number of the plurality of the discharge lamps installed in the processing apparatus and illuminating the remaining discharge lamps; and varying a combination of the discharge lamps to be deilluminated and illuminated, in accordance with the passage of time. By thus illuminating just a specific number of the discharge lamps, smaller than the total number of the discharge lamps installed in the processing apparatus, in a thinned-out fashion (thinned-out illumination) and varying the combination of the selectively deilluminated and illuminated discharge lamps in accordance with the passage of time, i.e. using the discharge lamps by rotation, it is possible to significantly prolong a time period over which the discharge lamps can operate without collective replacement with new ones—i.e. defer a time when the collective replacement becomes necessary—, and thereby greatly save time and labor necessary for the replacement and maintenance of the discharge lamps, so that the ultraviolet ray irradiation apparatus is allowed to operate in good condition continuously for a longer time.

While the embodiments to be described herein represent the preferred form of the present invention, it is to be understood that various modifications will occur to those skilled in the art without departing from the spirit of the invention. The scope of the present invention is therefore to be determined solely by the appended claims.

BRIEF DESCRIPTION OF THE DRAWINGS

For better understanding of the object and other features of the present invention, its embodiments will be described in greater detail hereinbelow with reference to the accompanying drawings, in which.

DETAILED DESCRIPTION OF THE EMBODIMENTS

Figure 1:
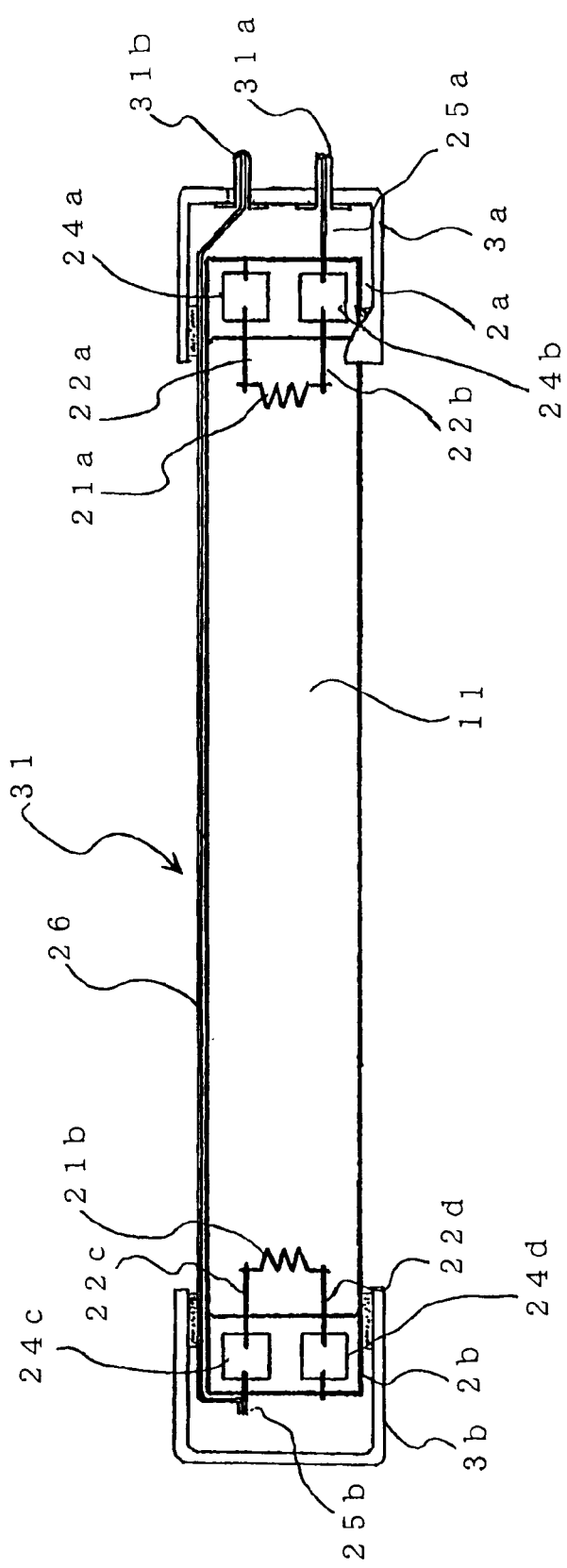
FIG. 1 is a sectional side view of a discharge lamp in accordance with an embodiment of the present invention.

FIG. 1 shows a discharge lamp in accordance with an embodiment of the present invention. First describing the basic construction of this discharge lamp 31, the discharge lamp 31 includes a light-emitting bulb or glass tube 11 made of synthetic quartz glass, a pair of filaments 21a and 21b disposed within and at opposite ends of the glass tube 11, seal sections 2a and 2b attached to the opposite ends of the glass tube 11, and bulb bases 3a and 3b attached to opposite ends of the discharge lamp 31. The filaments 21a and 21b each have coated thereon an emitter that is made, for example, of barium oxide. The filament 21a is held by a pair of inner leads 22a and 22b projecting inwardly from the seal section 2a, and similarly the other filament 21b is held by a pair of inner leads 22c and 22d projecting inwardly from the seal section 2b. The bulb bases 3a and 3b are each made of ceramics, and one of the bulb bases 3a is provided with a pair of electric terminals 31a and 31b. The seal sections 2a and 2b function to electrically connect the filaments 21a, 21b and the electric terminals 31a, 31b via outer leads 25a, 25b and 26 while keeping gas tightness by means of molybdenum films 24a–24d. Mercury of about 20 mg in weight and rare gas of about 400 Pa are sealed together in the glass tube 11. In the illustrated example of FIG. 1, the discharge lamp 31 is constructed as a two-terminal type discharge lamp, although the invention is not necessarily limited to the two-terminal type. Namely, one of the filaments 21a is connected at its one end to the electric terminal 31a via the inner lead 22b, molybdenum film 24b and outer lead 25a, while the other filament 21b is connected at its one end to the other electric terminal 31b via the inner lead 22c, molybdenum film 24c and outer leads 25a and 26.

The discharge lamp 31 in accordance with the instant embodiment is characterized in that the glass tube 11 is made of synthetic quartz glass and various dimensions of the discharge lamp 31, such as the inside diameter of the bulb or glass tube and distance between the filaments (filament-to-filament distance), are set on the basis of a predetermined condition such that ultraviolet rays of a 185 nm wavelength can be emitted with an enhanced efficiency. More specifically, the discharge lamp 31 in accordance with the instant embodiment is characterized in that various numerical values of the lamp 31 are set so as to be expressed by the following mathematical expression, assuming that the inside diameter D of the glass tube 11 made of quartz glass is 8 mm or over, the distance between the filaments 21a and 21b (filament-to-filament distance) is L (cm), voltage during illumination of the lamp (lamp voltage) is V (V: volt) and lamp current during illumination of the lamp is I (A: ampere):

$$(V-Vf)/L = X(\sqrt{D} \cdot \sqrt{I})$$

where $2.6 \leq X \leq 4.2$. Here, "Vf" represents a voltage drop at an anode (hereinafter also referred to as an "anode voltage drop") that is a factor (constant factor) depending solely on a illuminating power source employed. Also assume here that if the discharge lamp 31 is illuminated by a high-frequency power source of 1 kHz or over, Vf is 10 (Vf=10), but if the discharge lamp 31 is illuminated by a power source of 1 kHz or below, Vf is 50 (Vf=50).

The following paragraphs explain reasons why the above-mentioned mathematical expression has been derived as the condition for allowing ultraviolet rays of a 185 nm wavelength to be emitted with a high efficiency.

The inventor of the present invention and the like prepared a plurality of the low-pressure mercury vapor discharge lamps 31 of various sizes each having the basic construction as shown in FIG. 1, and conducted various experiments on these low-pressure mercury vapor discharge lamps 31 to evaluate relationship between electrical characteristics of the discharge lamps 31 and intensity of the 185 nm-wavelength ultraviolet rays emitted therefrom. Specifically, the low-pressure mercury vapor discharge lamps 31 employed in the experiments had synthetic quartz glass tubes which have respective inside diameters of 8 mm, 13 mm, 18 mm and 23 mm, wall thickness of 1 mm and lengths of 100–160 cm. Further, in these discharge lamps 31, the filament-to-filament distance L (cm) was set to 95–153 cm. The discharge lamps 31 to be tested were each inserted in a T-shaped glass tube having a branch tube attached to a central portion thereof for measuring intensity of 185 nm-wavelength ultraviolet rays. The interior of the T-shaped glass tube was filled with a nitrogen atmosphere, and cooling water was caused to flow along the outer surface of the T-shaped glass tube. Further, the illuminating power source was provided with two types of ballasts, an electronic ballast of about 40 kHz and an electromagnetic ballast of a commercial frequency, and five different current levels of 0.4 A (ampere), 0.6 A, 0.8 A, 1.0 A and 1.4 A were set, as the lamp current during illumination, for the discharge lamps 31. In this case, the 185 nm-wavelength ultraviolet rays were measured using an ultraviolet ray intensity meter "UV-185" (trademark) commercially available from ORC Manufacturing Co., Ltd., Tokyo, Japan.

Under the above-mentioned conditions, measurement was made of various electrical characteristics of each of the discharge lamps, namely, lamp voltage V, lamp current I, lamp power and intensity of the 185 nm-wavelength ultraviolet rays, while keeping the supplied current substantially constant and varying the temperature of the cooling water. The reason for varying the temperature of the cooling water is to change the mercury vapor pressure, i.e. to clarify relationship between the mercury vapor pressure and the radiation efficiency of the 185 nm-wavelength ultraviolet rays and electrical characteristics because the radiation efficiency of the 185 nm-wavelength ultraviolet rays and electrical characteristics are considered to depend on the mercury vapor pressure. By varying the temperature of the cooling water, the temperature of a coldest section of the discharge lamp, where superfluous mercury stays, can be changed, with the result that the mercury vapor pressure can be changed. Because the lamp voltage depends on the mercury vapor pressure, i.e. amount of mercury vaporization, within the discharge lamp, changing the temperature of the coldest section of the discharge lamp as noted above can variably set the lamp voltage V. In a discharge lamp of a given physical size, the lamp current I is also a constant factor determined by a ballast used, and so the lamp voltage V is a main factor that can control the intensity of the 185 nm-wavelength ultraviolet rays. Therefore, by varying the temperature of the cooling water to thereby variously change the value of the lamp voltage V and measuring not only the various values of the lamp voltage V but also the intensity values of the 185 nm-wavelength ultraviolet rays corresponding to the various values of the lamp voltage V, it is possible to identify correlation between the intensity of the 185 nm-wavelength ultraviolet rays and the lamp voltage V under the settings pertaining to the above-mentioned physical sizes and predetermined lamp current I. Therefore, the measurement is conducted in the manner noted above.

The measure of the intensity of the 185 nm-wavelength ultraviolet rays was processed from the viewpoint of "ultraviolet ray intensity per electric power consumed"; namely, the measured intensity value of the 185 nm-wavelength ultraviolet rays was divided by the measured value of the lamp current, and the resultant quotient was set as an index of "radiation efficiency" for the 185 nm-wavelength ultraviolet rays. Further, the measure of the lamp voltage was processed from the viewpoint of "voltage per unit length"; namely, the fixed value of the anode voltage drop Vf (V) was subtracted from the measured value of the lamp voltage V (V), and the resultant difference "V−Vf" was divided by the filament-to-filament distance L. The resultant quotient was set as a "potential inclination", i.e. as a lamp voltage per unit length of the filament-to-filament distance. Namely, by converting the "measured intensity value of the 185 nm-wavelength ultraviolet rays" and "lamp voltage V" into the "radiation efficiency of the 185 nm-wavelength ultraviolet rays" and "potential inclination" (lamp voltage per unit length of the filament-to-filament distance), respectively, the value of the "radiation efficiency of the 185 nm-wavelength ultraviolet rays" can be compared to each individual value of the "potential inclination", so that it is possible to approximately determine conditions for achieving a high radiation efficiency of the 185 nm-wavelength ultraviolet rays. Similarly to the above-mentioned, also assume here that if the discharge lamp is illuminated by a high-frequency power source of 1 kHz or over, the anode voltage drop Vf is 10 (Vf=10), but if the discharge lamp is illuminated by a power source of 1 kHz or below, the anode voltage drop Vf is 50 (Vf=50).

Figure 2:
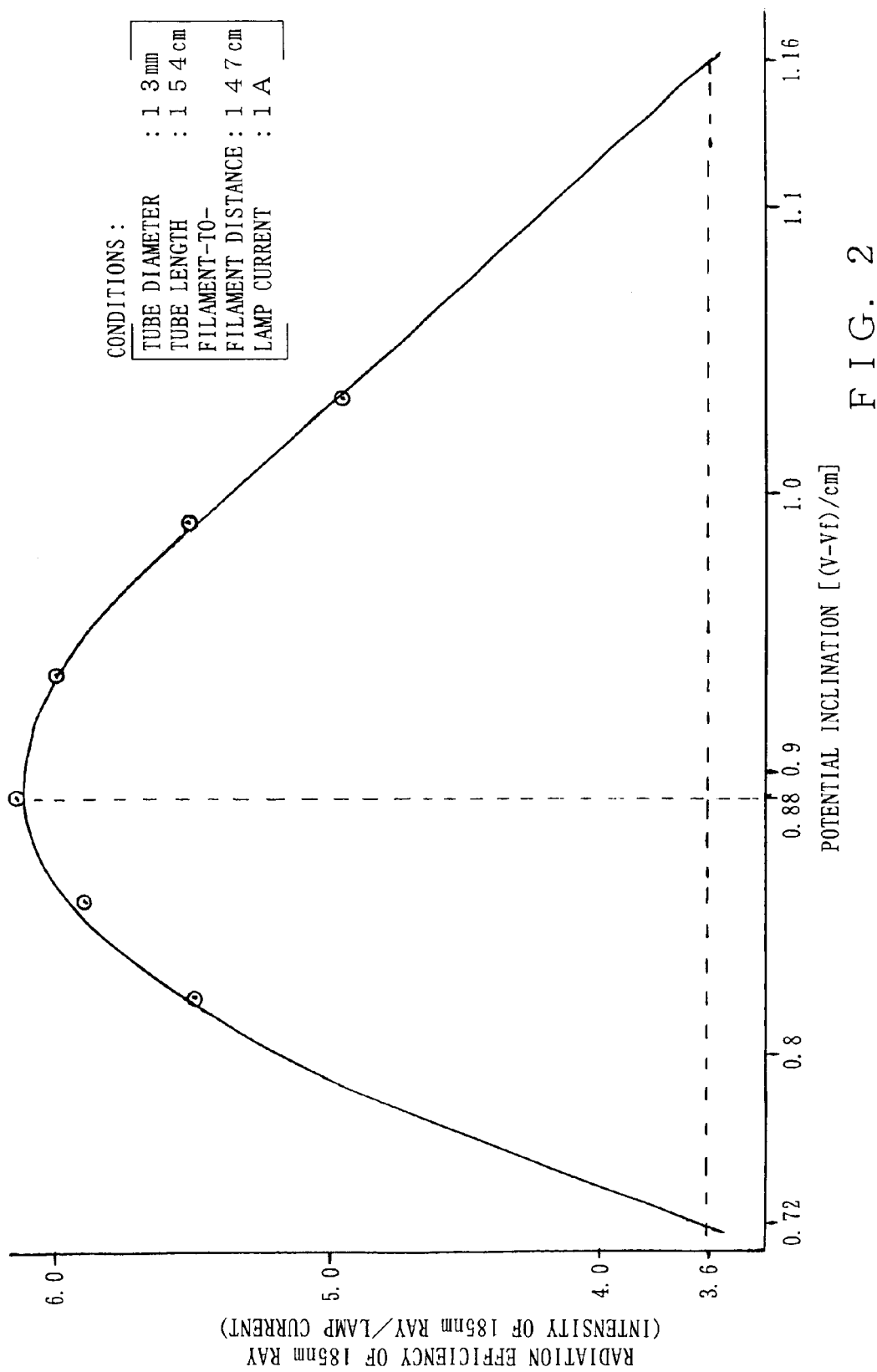
FIG. 2 is a graph showing an example of relationship between a "potential inclination" and "radiation efficiency of 185 nm-wavelength ultraviolet rays" derived on the basis of results of an experiment conducted on the discharge lamp of the present invention.

FIG. 2 shows measured results of the "potential inclination" and "radiation efficiency of the 185 nm-wavelength ultraviolet rays" under such physical conditions that the discharge lamp using a quartz glass tube of a 1 mm wall thickness has an inside diameter of 13 mm, tube length of 154 cm and filament-to-filament distance of 147 cm and under such electrical conditions that the lamp current I is 1A (ampere) and the electronic ballast is of about 40 kHz (namely, the anode voltage drop Vf=10). The measured results are plotted in the figure with the horizontal axis representing the value of the "potential inclination" and the vertical axis representing the value of the "radiation efficiency of the 185 nm-wavelength ultraviolet rays". The lamp voltage V was changed by changing the temperature of the cooling water as noted above. From FIG. 2, it can be seen that the "radiation efficiency of the 185 nm-wavelength ultraviolet rays" presents a highest value (about "6") when the "potential inclination" is about 0.88 (V/cm). This means that by just setting the various physical and electronic conditions such that the "radiation efficiency of the 185 nm-wavelength ultraviolet rays" falls within an appropriate admissible range including the highest or peak value (about "6" in the illustrated example of FIG. 2), there can be provided a highly-improved discharge lamp and ultraviolet ray irradiation apparatus capable of irradiating 185 nm-wavelength ultraviolet rays with a high efficiency. Observation of actual ultraviolet-ray irradiating states showed that it is proper to include, in the admissible range, values ranging from 100% to about 60–70% of the peak value of the the "radiation efficiency of the 185 nm-wavelength ultraviolet rays". Regarding the instance of FIG. 2, it can be said that desired efficient radiation of the 185 nm-wavelength ultraviolet rays is achievable as long as the value of the "radiation efficiency of the 185 nm-wavelength ultraviolet rays" is at least about 3.6 or over. In this case, it can be seen from the figure that the various conditions only have to be set in such a manner as to allow the "potential inclination" to fall within a range of about 0.72–1.16.

Figure 3:
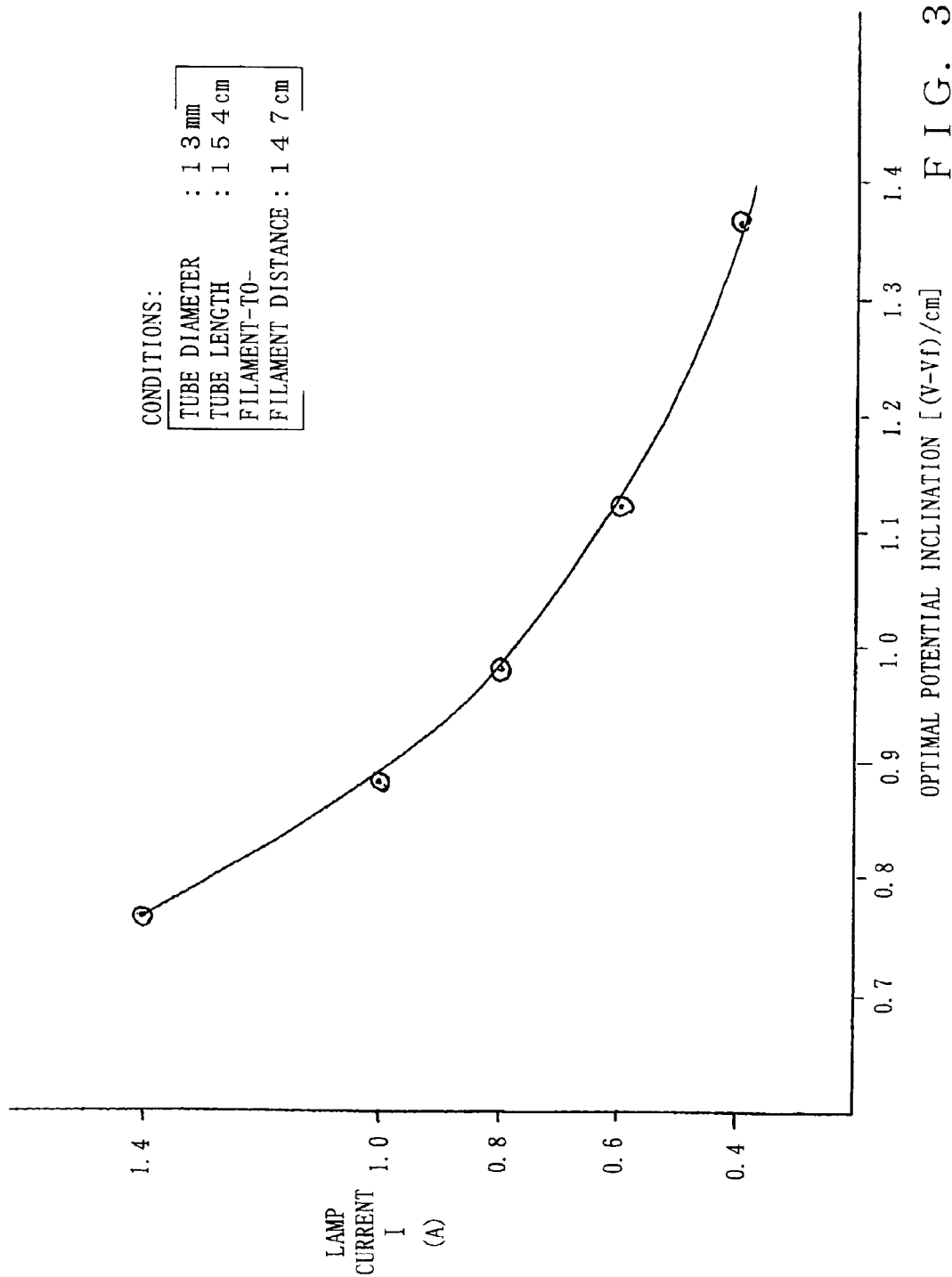
FIG. 3 is a graph showing an example of relationship between a "lamp current" and "potential inclination" derived on the basis of an experiment conducted on the discharge lamp of the present invention.
Figure 4:
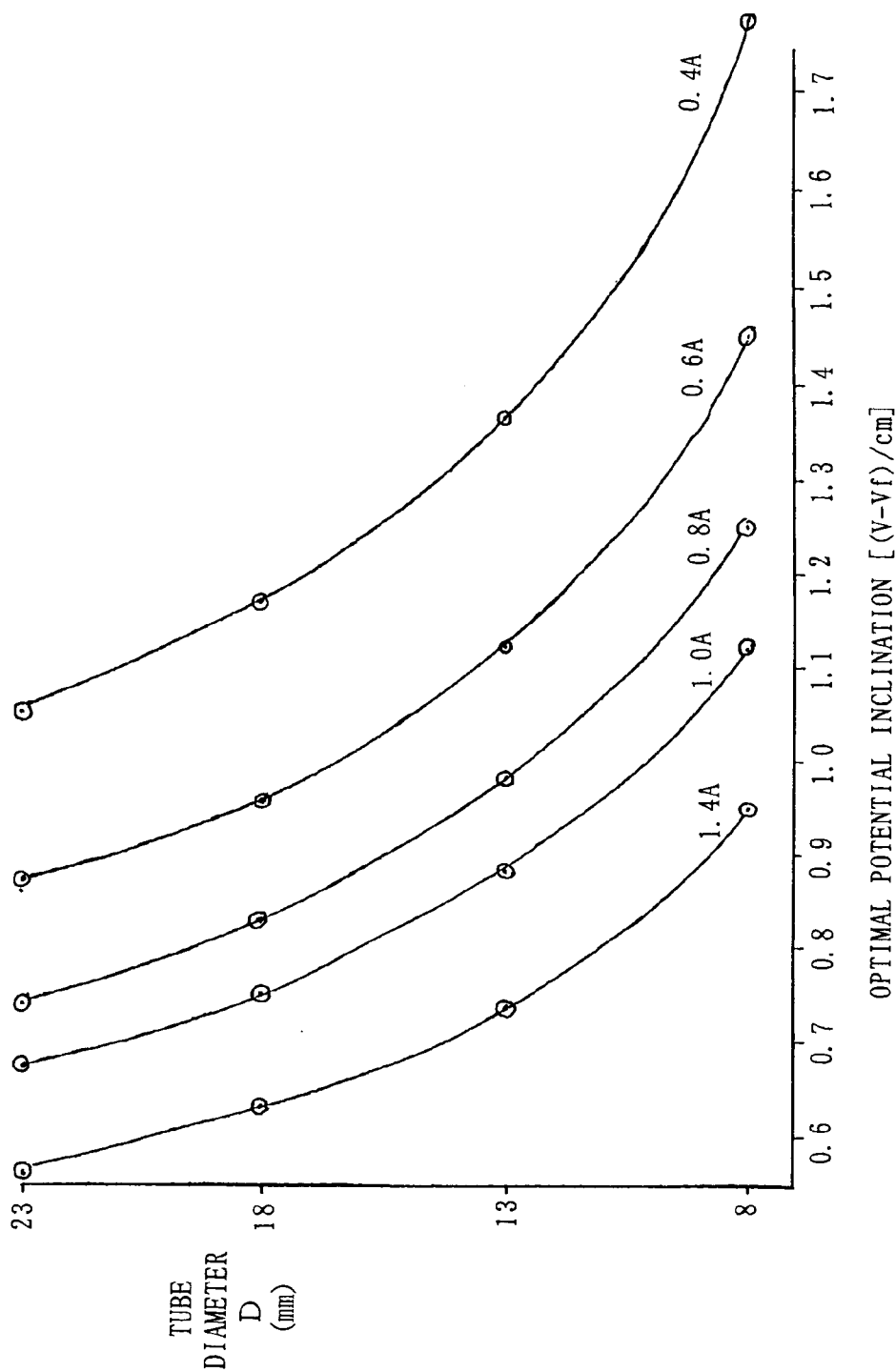
FIG. 4 is a graph showing an example of relationship between an inside diameter of a glass tube and an optimal "potential inclination" derived on the basis of results of an experiment conducted on the discharge lamp of the present invention, in correspondence with various values of the "lamp current"

The following paragraphs describe other measured results. Namely, regarding a discharge lamp having an inside diameter of 13 mm, tube length of 154 cm and filament-to-filament distance of 147 cm like the one shown in FIG. 2, a search was made, while variously varying the value of the lamp current I, for an optimal potential inclination for each of the lamp current values which achieves the highest or peak value of the "radiation efficiency of the 185 nm-wavelength ultraviolet rays". FIG. 3 is a graph showing the thus-obtained "optimal potential inclination" (plotted on the horizontal axis) for each of the various lamp current values (plotted on the vertical axis). From FIG. 3, it can be seen that the "optimal potential inclination" is almost in inverse proportion to the square root of the lamp current value (I)(i.e., √I).

Then, in a similar manner to the above-described, a search was made for an optimal "potential inclination" which achieves the highest or peak value of the "radiation efficiency of the 185 nm-wavelength ultraviolet rays", for all of the discharge lamps of the above-mentioned sizes employed in the experiments, as a result of which it was found that the optimum "potential inclination" was almost in inverse proportion to the square root of the lamp current value (I)(i.e., √I) for every one of the tube diameters. Further, as a result of plotting the optimum "potential inclination" with the tube diameter (D) used as a parameter, it was found that the optimum "potential inclination" was also almost in inverse proportion to the square root of the tube diameter (D). Namely, when the discharge lamp having a tube diameter (D) in a range of 8–23 mm was operated with a lamp current in a range of 0.4–1.4 A, it was found that the optimum "potential inclination" for achieving the maximum radiation efficiency of the 185 nm-wavelength ultraviolet rays was inversely proportional to the square roots of the tube diameter (D) and current (I) (i.e., √D and √I). This is true irrespective of which one of the high-frequency electronic ballast and commercial-frequency electromagnetic ballast is used, if only the factor of the illuminating current is taken into consideration.

From the foregoing, it is evident that the "potential inclination", i.e. "(V−Vf/L)" is in inverse proportional relation to the square root of the tube diameter D (i.e., √D) and the square root of the lamp current I (i.e., √I). If the proportionality constant is X, the optimal potential inclination (i.e., (V−Vf)/L) can be represented by $$(V-Vf)/L = X/(\sqrt{D} \cdot \sqrt{I})$$

Because the inside diameter D was set to 13 mm and the lamp current I was set to 1 A in the instance of FIG. 2, "√D·√I" is about 3.605. Thus, in order to allow the "potential inclination" to fall within the above-mentioned admissible range of about 0.72–1.16, it is only necessary that the proportionality constant X take a value approximately in the range of $2.6 \leq X \leq 4.2$.

In view of the above-described experimental results, the inventor of the present invention has come to the conclusion that, in the discharge lamp 31 which employs the glass tube 11 made of synthetic quartz glass as shown in FIG. 1 and where the inside diameter D (measured in mm) of the synthetic quartz glass tube 11 is set to 8 mm or more, the distance between the filaments 21a and 21b (filament-to-filament distance) is set to L (measured in cm) and the lamp voltage and current during illumination are set to V (measured in V (volts)) and I (measured in A (amperes)), respectively, it is most appropriate to set the conditions for efficiently irradiating the 185 nm-wavelength ultraviolet rays such that the individual values have relationship represented by the following mathematical expression:

$$(V-Vf)/L = X/(\sqrt{D} \cdot \sqrt{I}), \text{ provided that } 2.6 \leq X \leq 4.2$$

Similarly to the above-mentioned, assume here that the anode voltage drop Vf determined solely by the illuminating power source is 10 (i.e., Vf=10) if the discharge lamp is illuminated by a high-frequency power source of 1 kHz or over, but 50 (i.e., VF=50) if the discharge lamp is illuminated by a power source of 1 kHz or below.

As described, the present invention is characterized in that synthetic quartz glass is used as the light emitting bulb or tube of the discharge lamp. The synthetic quartz glass is manufactured using silicon tetrachloride as its starting material, contains an extremely small amount of impurities, and has a good transmissivity with respect to ultraviolet rays of short wavelengths. Although the above-mentioned "relationship among the potential inclination, tube diameter and lamp current for achieving the maximum radiation efficiency of the 185 nm-wavelength ultraviolet rays" is not necessarily applicable to the synthetic quartz glass alone, it should be note that a light emitting tube made of ordinary (i.e., natural) quartz glass can hardly bear practical use, because the transmissivity with respect to the 185 nm-wavelength ultraviolet rays in decreases dramatically in the case of the light emitting tube made of natural quartz glass. Specifically, in the case where the light emitting tube is made of ordinary (natural) quartz glass, the glass tube, which inherently has a low transmissivity with respect to ultraviolet rays of short wavelengths, absorbs more 185 nm-wavelength ultraviolet rays as the radiation efficiency for 185 nm wavelength increases, so that the glass itself changes in quality to produce cloudiness or opacity and thus the transmissivity with respect to the 185 nm-wavelength ultraviolet rays decreases due to the opacity. It is thus considered that there would occurs a repetition of the cycle of further transmissivity decrease and quality change and this repetition of the cycle results in a rapid decrease in the transmissivity with respect to the 185 nm-wavelength ultraviolet rays. Therefore, it is essential for the present invention to employ the synthetic quartz glass tube.

The organic-substance decomposing apparatus, i.e. ultraviolet ray irradiation apparatus, employing the discharge lamp of the present invention is suitably applicable to, for example, production of ultrapure water for use in semiconductor manufacture. In such a case, the ultraviolet ray irradiation apparatus must stand long-time continuous operation for one to three years. Because the synthetic quartz glass has a superior transmissivity with respect to ultraviolet ray at its initial stage of use life and contains a very small amount of impurities that would become a main cause of quality change, it can keep a high radiation efficiency of ultraviolet rays even when the ultraviolet ray irradiation apparatus is operated in an environment where the radiation rate of 185 nm-wavelength ultraviolet rays is high. It should be obvious that the ultraviolet ray irradiation apparatus employing the discharge lamp of the present invention is applicable to a variety of fields, other than the semiconductor manufacturing, that require decomposition, sterilization, disinfection, etc. of organic substances, such as beverage manufacture, food manufacture, medical treatment, water processing, etc.

Figure 5:
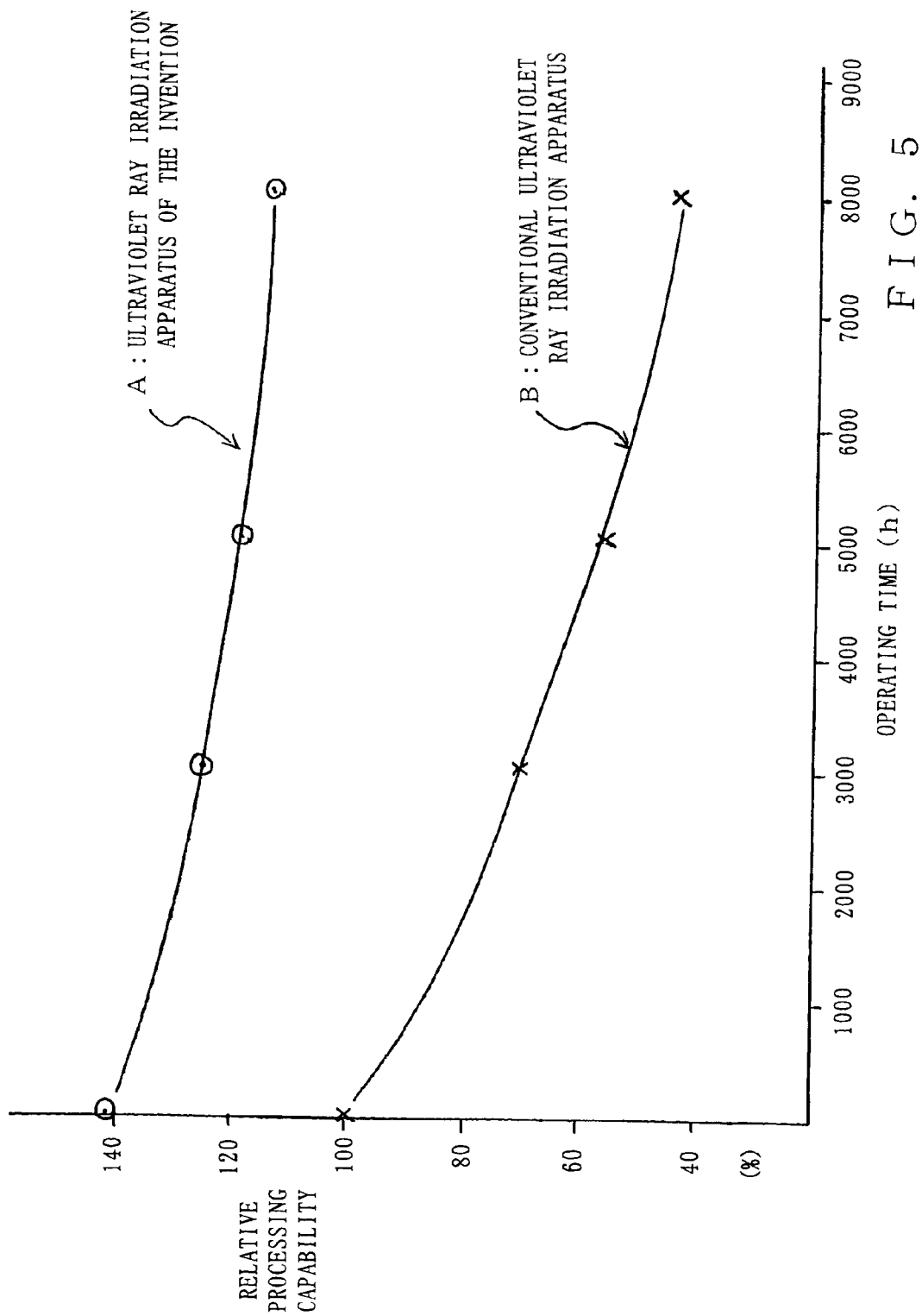
FIG. 5 is a graph showing results of an experiment on variations over time of a processing capability of an ultraviolet ray irradiation apparatus employing the discharge lamps of the present invention, in comparison with variations over time of a processing capability of a conventional ultraviolet ray irradiation apparatus.
Figure 6:
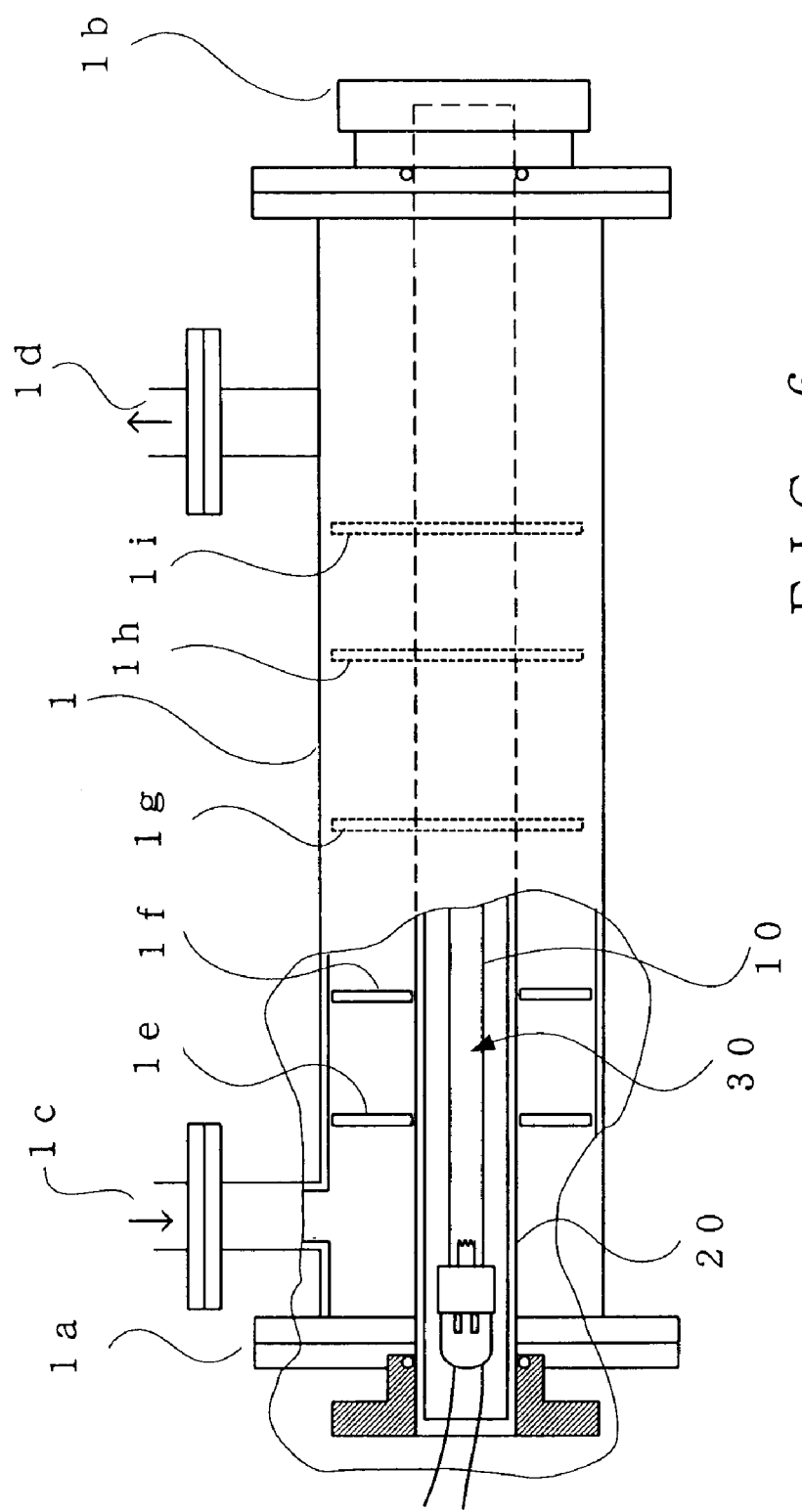
FIG. 6 is a sectional side view of an example of a conventional ultraviolet ray irradiation apparatus employing provided with conventional discharge lamps.

FIG. 5 is a graph showing actual measured data obtained by use of a conventional ultraviolet ray irradiation apparatus B provided with a conventional discharge lamp and the ultraviolet ray irradiation apparatus A provided with the discharge lamp of the present invention. More specifically, FIG. 5 comparatively shows the processing capabilities of the two apparatus in processing raw water having a TOC (Total Organic Carbon) density of 10 ppb into water of 1 ppb or below, in terms of a flow rate per unit power consumption amount. In the figure, a value representing the processing capability of the conventional ultraviolet ray irradiation apparatus B at its initial stage of use is given as 100%. From the graph, it can been seen that there is a great difference in performance between the conventional ultraviolet ray irradiation apparatus B and the ultraviolet ray irradiation apparatus A of the invention at the initial stage and this performance difference increases as the time passes. It was confirmed that if the processing capability of the conventional ultraviolet ray irradiation apparatus B provided with the conventional discharge lamp after use of 8,500 hours, which is generally an average total time of use of the apparatus per year, is represented as "1", the processing capability of the ultraviolet ray irradiation apparatus A provided with the discharge lamp of the present invention is about 2.5 times higher. As noted above, the ultraviolet ray irradiation apparatus employed in this field are normally intended for long-time continuous operation for one to three years. Also, there is an increasing need among users for maintenance-free operation throughout the expected continuous operating time. Therefore, the high processing capability as set forth above also allows the ultraviolet ray irradiation apparatus to operate while effecting thinned-out illumination of the discharge lamps, which could advantageously lead to saving in maintenance as well as in energy as will be explained below.

Namely, explaining an example of a method for using or operating the ultraviolet ray irradiation apparatus A provided with the discharge lamp of the present invention, a plurality of the discharge lamps are installed in a processing apparatus that uses the discharge lamps to perform processes, such as organic-substance decomposition, sterilization, disinfection, etc., on a predetermined object to be processed (liquid, solid object or the like). Then, the so-called thinned-out illumination is carried out by deilluminating a predetermined number of the installed discharge lamps and illuminating only the remaining discharge lamps, and the combination of the selectively deilluminated and illuminated discharge lamps is varied as appropriate in accordance with the passage of time. By thus illuminating only some of the installed discharge lamps in a thinned-out fashion and varying the combination of the selectively illuminated discharge lamps with the passage of time, it is possible to significantly prolong a time period over which the discharge lamps can operate without collective replacement with new ones (i.e. delay a time when the collective replacement of the discharge lamps becomes necessary) and thereby save time and labor necessary for the replacement and maintenance of the discharge lamps, so that the ultraviolet ray irradiation apparatus is allowed to operate in good condition continuously for a longer time. Considering that if the discharge lamps of the present invention capable of high-efficiency radiation are employed, even those ultraviolet ray irradiation apparatus, which used to install and illuminate all of n (n is an arbitrary integral number greater than 2) conventional-type discharge lamps of poor radiation efficiency, can achieve necessary and sufficient processed results by just illuminating m, smaller than n, discharge lamps of the invention, another example of the method for using the ultraviolet ray irradiation apparatus is possible which constructs an ultraviolet ray irradiation apparatus by installing n (the same number as in the conventional technique) discharge lamps of the invention capable of high-efficiency radiation, more than the m discharge lamps to be illuminated concurrently, and illuminates the n discharge lamps in the thinned-out fashion.

As set forth above, the present invention has been made, with a view to enhancing the radiation efficiency of the 185 nm-wavelength ultraviolet rays in the low-pressure mercury vapor discharge lamp and maintaining the enhanced radiation efficiency, by making the light-emitting tube of synthetic quartz glass in stead of ordinary (natural) quartz glass and discovering relationship, preferable for attaining the enhanced radiation efficiency, between the dimensional characteristics of the inside diameter D of the light-emitting tube and filament-to-filament distance L and the electrical characteristics of the lamp current I and lamp voltage V.

Thus, the discharge lamp itself may be of any other construction than the type shown in FIG. 1, as long as it satisfies the requirements of the characteristics of the present invention. For example, whereas the embodiments of the invention have been described above in relation to the discharge lamp having metal mercury sealed therein, it should be appreciated that a discharge lamp having sealed therein an amalgam of mercury and other metal can achieve the same advantageous results as discussed above. Also, operation and advantageous results, similar to those discussed above, can be obtained by a continuous-heating type discharge lamp that constantly heats the filaments, or a discharge lamp of a type having filaments and anode provided in parallel, or a two-base type discharge lamp having charging pins projecting outwardly from opposite ends thereof, as long as the discharge lamp is a low-pressure mercury vapor discharge lamp. Of course, the discharge lamp may include four terminals or the like rather than the two terminals 31a and 31b as shown in FIG. 1.

In summary, the present invention arranged in the above-mentioned manner can enhance the radiation efficiency of 185 nm-wavelength ultraviolet rays and keep the enhanced radiation efficiency of the 185 nm-wavelength ultraviolet rays. The present invention also permits effective savings in energy and maintenance.

What is claimed is:

1. A low-pressure mercury vapor discharge lamp comprising:
   a synthetic quartz glass tube having an inside diameter D;
   a pair of filaments provided within and at opposite ends of said glass tube, said filaments being spaced apart by a distance L; and
   a mixture of rare gas and metal, including at least mercury, sealed inside said glass tube,
   wherein the lamp radiates ultraviolet rays of a 185 nm wavelength at an enhanced efficiency, while providing a longer life, by satisfying the following expression:

$$(V-V_f)/L = X/(\sqrt{D} \cdot \sqrt{I}),$$

where $2.6 \leq X \leq 4.2$, $V_f$ is a voltage drop of 10 or 50, respectively, at an anode if a power source applied is 1 kHz or over, or 1 kHz or below, D is 8 mm or greater, and V and I are respectively voltage and current applied to illuminate the discharge lamp.

2. An ultraviolet ray irradiation apparatus for irradiating ultraviolet rays onto an object having a low-pressure mercury vapor discharge lamp, the discharge lamp comprising:
   a synthetic quartz glass tube having an inside diameter D;
   a air of filaments provided within and at opposite ends of said lass tube said filaments being spaced apart by a distance L; and
   a mixture of rare gas and metal, including at least mercury, sealed inside said glass tube,
   wherein the lamp radiates ultraviolet rays of a 185 nm wavelength at an enhanced efficiency, while providing a longer life, by satisfying the following expression:

$$(V-V_f)/L = X/(\sqrt{D} \cdot \sqrt{I}),$$

where $2.6 \leq X \leq 4.2$, $V_f$ is a voltage drop of 10 or 50, respectively, at an anode if a power source applied is 1 kHz or over, or 1 kHz or below, D is 8 mm or greater, and Vend I are respectively voltage and current applied to illuminate the discharge lamp.

3. A method of using said ultraviolet ray irradiation apparatus having a plurality of one low-pressure mercury vapor discharge lamps each comprising: a synthetic quartz glass tube having an inside diameter D; a pair of filaments provided within and at opposite ends of said glass tube, said filaments being spaced apart by a distance L; and a mixture of rare gas and metal, including at least mercury, sealed inside said glass tube, wherein the lamp radiates ultraviolet rays of a 185 nm wavelength at an enhanced efficiency, while providing a longer life by satisfying in the following expression:

$$(V-V_f)/L = X/(\sqrt{D} \cdot \sqrt{I}),$$

where $2.6 \leq X \leq 4.2$, $V_f$ is voltage drop of 10 or 50, respectively, at an anode if a power source applied is 1 kHz or over, or 1 kHz or below, D is 8 mm or greater, and V and I are respectively voltage and current applied to illuminate the discharge lamp, the method comprising the steps of:

illuminating only a predetermined number of said discharge lamps; and varying the combination of said discharge lamps to be illuminated, in accordance with passage of time.

* * * * *

UNITED STATES PATENT AND TRADEMARK OFFICE
CERTIFICATE OF CORRECTION

PATENT NO. : 6,683,411 B2
DATED : January 27, 2004
INVENTOR(S) : Koji Nakano

It is certified that error appears in the above-identified patent and that said Letters Patent is hereby corrected as shown below:

Title page,
Item [57], ABSTRACT,
Line 8, please delete "D (cm)" and insert -- D (mm) --.

Column 2,
Line 30, please delete "(cm)" and insert -- (mm) --.

Signed and Sealed this

Twenty-seventh Day of April, 2004

JON W. DUDAS
*Acting Director of the United States Patent and Trademark Office*